US009078876B2

(12) United States Patent
Ehrhardt et al.

(10) Patent No.: US 9,078,876 B2
(45) Date of Patent: *Jul. 14, 2015

(54) METHOD FOR TREATING PSORIASIS

(71) Applicant: Abbvie Biotherapeutics, Inc., Redwood City, CA (US)

(72) Inventors: Rolf O. Ehrhardt, Mill Valley, CA (US); Kenneth Hong, Millbrae, CA (US)

(73) Assignee: Abbvie Biotherapeutics, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/679,022

(22) Filed: Nov. 16, 2012

(65) Prior Publication Data

US 2013/0071388 A1    Mar. 21, 2013

Related U.S. Application Data

(63) Continuation of application No. 10/108,191, filed on Mar. 26, 2002, now abandoned, which is a continuation of application No. 09/457,912, filed on Dec. 8, 1999, now Pat. No. 6,410,824.

(60) Provisional application No. 60/111,642, filed on Dec. 9, 1998.

(51) Int. Cl.
| *A61K 39/395* | (2006.01) |
| *A61K 38/19* | (2006.01) |
| *C07K 16/24* | (2006.01) |
| *C07K 14/54* | (2006.01) |
| *A61K 39/00* | (2006.01) |
| *A61K 38/20* | (2006.01) |
| *A01K 67/027* | (2006.01) |
| *A61K 35/12* | (2015.01) |

(52) U.S. Cl.
CPC ......... *A61K 39/3955* (2013.01); *A01K 67/0271* (2013.01); *A61K 38/208* (2013.01); *A61K 39/00* (2013.01); *C07K 14/5434* (2013.01); *C07K 16/24* (2013.01); *C07K 16/244* (2013.01); *A61K 35/12* (2013.01); *A61K 2039/505* (2013.01); *C07K 2316/96* (2013.01); *C07K 2317/76* (2013.01)

(58) Field of Classification Search
CPC ............ A61K 39/00; A61K 2039/505; A61K 2039/55538; A61K 38/208; C07K 16/244; C07K 14/54

See application file for complete search history.

(56) References Cited

U.S. PATENT DOCUMENTS

| 4,362,155 A | 12/1982 | Skurkovich |
| 4,824,432 A | 4/1989 | Skurkovich et al. |
| 4,897,264 A | 1/1990 | Novick et al. |
| 5,451,658 A | 9/1995 | Seelig |
| 5,554,515 A | 9/1996 | Kurimoto et al. |
| 5,578,707 A | 11/1996 | Novick et al. |
| 5,632,988 A | 5/1997 | Ingram et al. |
| 5,780,027 A | 7/1998 | Maroun |
| 6,036,956 A | 3/2000 | Jacob et al. |
| 6,333,032 B1 | 12/2001 | Skurkovich et al. |
| 6,350,860 B1 | 2/2002 | Buyse et al. |
| 2002/0025316 A1 | 2/2002 | Ferguson |
| 2003/0012787 A1 | 1/2003 | Ashkenazi et al. |
| 2003/0044410 A1 | 3/2003 | Skurkovich et al. |

FOREIGN PATENT DOCUMENTS

| CA | 2191870 | 7/1995 |
| CA | 2224256 | 12/1997 |
| CA | 2275692 | 12/1997 |
| CA | 2297692 | 8/1998 |
| EP | 0 304 291 | 2/1989 |
| EP | 0 485 471 | 8/1990 |
| EP | 0 387 095 | 9/1990 |
| EP | 0 659 766 | 6/1995 |
| EP | 0 695 189 | 2/1996 |
| EP | 0 845 007 | 8/1996 |
| JP | 08 289699 | 11/1996 |
| WO | WO 88/07869 | 10/1988 |
| WO | WO 92/11018 | 7/1992 |
| WO | WO 96/34096 | 10/1996 |
| WO | WO 96/40093 | 12/1996 |
| WO | WO 97/07136 | 2/1997 |

(Continued)

OTHER PUBLICATIONS

Yawalkar et al. (J Invest Dermatol. Dec. 1998;111(6):1053-7).*
Advanced Biotherapy, Inc., Press Release, "Advanced Biotherapy, Inc. Discloses Results of Pilot Study and Patent Pending for Exclusive Use of Antibodies to Gamma interferon for the Treatment of Pemphigus Vulgaris", http://www.Advancedbiotherapy.com/press_release_11_26_02.htm.
Bach, "Anti-gamma interferon (IFN-γ) monoclonal antibodies", Monoclonal Antibodies and Peptide Therapy in Autoimmune Diseases, Bach ed., Marcel Dekker, Inc. New York, NY (1993).
Baker et al., "Induction of cutaneous lymphocyte-associated antigen expression by group A streptococcal antigens in psoriasis", Arch. Dermatol. Res., 289: 671-676 (1997).
Barrett et al., "Interferon-gamma is required during the initiation of an organ-specific autoimmune disease", Eur. J. Immunol., 26(7): 1652-1655 (1996).

(Continued)

*Primary Examiner* — Robert Landsman
*Assistant Examiner* — Bruce D Hissong
(74) *Attorney, Agent, or Firm* — Leon R. Yankwich; David G. O'Brien; Yankwich & Associates, P.C.

(57) ABSTRACT

Methods and compositions are provided for the creation and screening of non-human animal models having many of the histologic characteristics of human psoriasis. Immunocompromised host animals are injected with a purified population of CD45Rb positive cells, which are tolerant of the host major histocompatibility antigens, but are mismatched at one or more minor antigens. The injected cells are stimulated with a pro-inflammatory cytokine, e.g. IL-12, and a polyclonal activating agent. The injected animals develop a chronic skin disorder that includes histological features observed in human psoriasis, e.g. rete pegs, severe acanthosis and infiltration of Th1 cells into the dermis.

7 Claims, 2 Drawing Sheets

(56) References Cited

FOREIGN PATENT DOCUMENTS

| WO | WO 97/37679 | 10/1997 |
|---|---|---|
| WO | WO 97/38093 | 10/1997 |
| WO | WO 98/16248 | 4/1998 |
| WO | WO 98/28001 | 7/1998 |
| WO | WO 99/09055 | 2/1999 |

OTHER PUBLICATIONS

Billau, "Interferon-γ in Autoimmunity", Cytokine and Growth Factor Reviews, 7(1): 25-34 (1996).
Billau, "Interferons in multiple sclerosis: warnings from experiences", Neurol., 45(6 Suppl. 6): S50-3 (1995).
Billau et al., "Enhancement of experimental allergic encephalomyelitis in mice by antibodies against IFN-gamma", J Immunol., 140(5): 1506-1510 (1988).
Campbell et al., "Essential role for interferon-gamma and interleukin-6 in autoimmune insulin-dependent diabetes in NOD/Wehi mice", J. Clin. Invest., 87(3): 739-742 (1991).
Debray-Sachs et al., "Prevention of diabetes in NOD mice treated with antibody to murine IFN gamma", J. Autoimmune, 4(2): 237-248 (1991).
Depla et al., "Anti-idiotypic and anti-ant-idiotype antibodies as highly specific tools in epitope and active site studies on human interferon-gamma", Mol. Immunol., 28(7): 743-751 (1991).
Funauchi et al., "Serum level of interferon-gamma in autoimmune diseases", Tohoku J. Exp. Med., 164(4): 259-267 (1991).
Haak-Frendscho et al., "Inhibition of interferon-gamma by an interferon-gamma receptor immunoadhesion", Immunol., 79(4): 594-599 (1993).
Hartung et al., "The role of interferon-gamma in the pathogenesis of experimental autoimmune disease of the peripheral nervous system", Ann. Neuro., 27(3): 247-257 (1990).
Heremans et al., "Chronic relapsing experimental autoimmune encephalomyelitis (CREAE) in mice enhancements by monoclonal antibodies against interferon-gamma", Eur. J. Immunol., 26: 2393-2398 (1996).
Hong et al., "IL-12, Independently of IFN-γ, Plays a Crucial Role in the Pathogenesis of a Murine Psoriasis-Like Skin Disorder", J. Immunol., 162(12): 7480-7491 (1999).
International Search Report EP03001299.1 Jul. 3, 2003.
Jacob et al., "In-vivo treatment of (NZB X NZW) F1 lupus-like nephritis with monoclonal antibody to gamma interferon", J. Exp. Med., 166(3): 798-803 (1987).
Kawakami et al., "Induction of experimental thyroiditis in mice by recombinant interferon gamma administration", Acta. Endocrinol., 122(1): 41-48 (1990).
Kay et al., "Overexpression of class 1 major histocompatibility complex accompanies insulitis in the non-obese diabetic mouse and is prevented by anti-interferon-gamma antibody", Diabetologia, 34(11): 779-785 (1991).
Kung et al., "Effects of Interferon-gamma therapy on thyroid function, T-lymphocyte subpopulations and induction of autoantibodies", J. Clin. Endocrinal. Metab., 71(5): 1230-1234 (1990).
Landolfi et al., "The integrity of the ball-and-socket joint between V and C domains is essential for complete activity of a humanized antibody", Journal of Immunology, 166(3): 1748-1754 (2001).
Lee et al., "Sensitization to self (virus) antigen by in situ expression of murine interferon-γ", Clin. Invest., 95(2): 486-492 (1995).
Lublin et al., "Monoclonal anti-gamma interferon antibodies enhance experimental allergic encephalomyelitis", Autoimmunity, 16(4): 267-274 (1993).
Moosmayer et al., "A bivalent immunoadhesin of the human interferon-gamma receptor is an effective inhibitor of IFN-gamma activity", J. Interferon Cytokine Res., 15(12): 1111-1115 (1995).
Nickoloff et al., "Animal Model for Psoriasis", Nature Medicine, 3(5): 475-476 (1997).
Nicollettti et al., "In vivo treatment with a monoclonal antibody to interferon-gamma neither affects the survival nor the incidence of lupus-nephritis in the NRL/lpr-lpr mouse", Immunopharmacol., 24(1): 11-16 (1992).
Ozmen et al., "Experimental therapy of systemic lupus erythematosus: the treatment of NZB/W mice with mouse soluble interferon-gamma receptor inhibits the onset of glomerulonephritis" Eur. J. Immunol., 25(1): 6-12 (1996).
Perez et al., "Antierythrocyte autoantibody formation after therapy with IL-2 and gamma-interferon", Cancer, 67(10): 2512-2517 (1991).
Prinz et al., "T cell clones from psoriasis skin lesions can promote keratinocyte proliferation in-vitro via secreted products", European Journal of Immunology, 24(3): 593-598 (1994).
Reeves, "Autoimmune mechanisms in psoriasis", Semin Dermatol., 10(3): 217-224 (1991).
Skurkovitch et al, "A unifying model of the Immunoregulatory Role of the Interferon System: Can Interferon Produce Disease in Humans?", Clin. Immunol. Immunopathol., 43: 362-373 (1987).
Skurkovitch et al., "Interferon Increases IgE Binding to Basophils", Annals of Allergy, 50: 305-308 (1983).
Skurkovitch et al., "The possible Participation of Interferon Inhibitor in the Formation of the Remission in Autoimmune Diseases and Allergy (Hypersensitivity of Immediate Type)", Medical Hypotheses, 7: 1189-1191 (1981).
Skurkovitch et al., "The Probable Role of Interferon in Allergy", Annals of Allergy, 35: 356-360 (1975).
Stoll et al., "Localization of interferon-gamma la-antigen in t cell line-mediated experimental autoimmune encephalitis", Am. J. Pathol., 142(6): 1866-1875 (1993).
Strigard et al., "In vivo treatment of rats with monoclonal antibodies against gamma interferon: effects on experimental allergic neuritis", Acta. Neuol. Scand., 80(3): 201-207 (1989).
Stull et al., "Induction of granulomatous experimental autoimmune thyroidits in mice with in vitro activated effector T cells and anti-IFN-gamma antibody", J. Immunol., 149(6): 2219-2226 (1992).
Takahashi, "Imbalance towards TH1 predominance is associated with acceleration of lupus-like autoimmune syndrome in MRL mice", J. Clin. Invest., 97(7): 1597-1604 (1996).
Tang et al., "The effects of monoclonoal antibody to interferon-gamma on experimental autoimmune thyroiditis (EAT): prevention of disease and decrease of EAT-specific T cells", Eur. J. Immunol., 23(1): 275-278 (1993).
Umland et al., "Effects of in vivo administration of interferon (INF)-gamma, anti-INF-gamma, or anti-interleukin-4 monoclonal antibodies in chronic autoimmune graft vs. host disease", Clin. Immunol. Immunopathol., 63(1): 66-73 (1992).
Van der Meide, "Susceptibility to mercuric chloride-induced glomerulonephritis is age-dependent: study of the role of the INF-gamma", Cell Immunol., 162(1): 131-137 (1995).
Wandl et al., "Lupus-like autoimmune disease induced by interferon therapy for myeloproliferative disorders", Clin. Immunol. Immunopathol., 65(1): 70-74 (1992).
Weber et al., "Induction of autoimmune phenomena in patients with chronic hepatitis B treated with gamma-interferon", J. Hepatol., 20(3): 321-328 (1994).
Wrone-Smith et al., "Dermal Injection of Immunocytes Induces Psoriasis", J. Clin. Invest., 98(9): 1878-1887 (1996).

\* cited by examiner

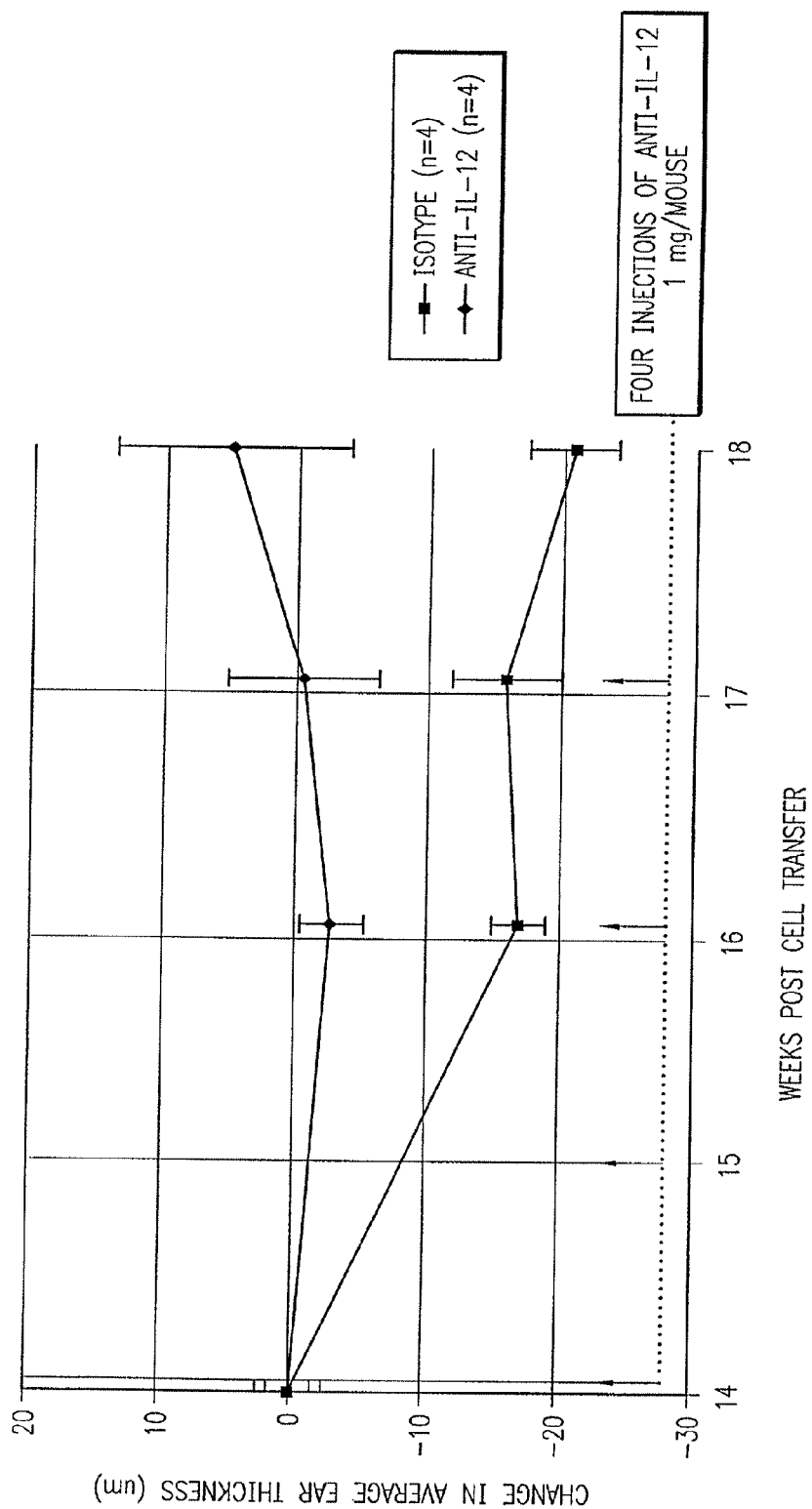

METHOD FOR TREATING PSORIASIS

CROSS-REFERENCE TO RELATED APPLICATIONS

This application is a continuation of U.S. application Ser. No. 10/108,191 filed Mar. 26, 2002 (pending) which is a continuation of U.S. application Ser. No. 09/457,912, filed Dec. 8, 1999 (now U.S. Pat. No. 6,410,824), which claims priority to U.S. Provisional Application No. 60/111,642, filed Dec. 9, 1998.

INTRODUCTION

1. Background

Psoriasis is a chronic skin disease, characterized by scaling and inflammation. Psoriasis affects 1.5 to 2 percent of the United States population, or almost 5 million people. It occurs in all age groups and about equally in men and women. People with psoriasis suffer discomfort, restricted motion of joints, and emotional distress. When psoriasis develops, patches of skin thicken, redden, and become covered with silvery scales, referred to as plaques. Psoriasis most often occurs on the elbows, knees, scalp, lower back, face, palms, and soles of the feet. The disease also may affect the fingernails, toenails, and the soft tissues inside the mouth and genitalia. About 10 percent of people with psoriasis have joint inflammation that produces symptoms of arthritis.

When skin is wounded, a wound healing program is triggered, also known as regenerative maturation. Lesional psoriasis is characterized by cell growth in this alternate growth program. In many ways, psoriatic skin is similar to skin healing from a wound or reacting to a stimulus such as infection, where the keratinocytes switch from the normal growth program to regenerative maturation. Cells are created and pushed to the surface in as little as 2-4 days, and the skin cannot shed the cells fast enough. The excessive skin cells build up and form elevated, scaly lesions. The white scale (called "plaque") that usually covers the lesion is composed of dead skin cells, and the redness of the lesion is caused by increased blood supply to the area of rapidly dividing skin cells.

The exact cause of psoriasis in humans is not known, although it is generally accepted that it has a genetic component, and a recent study has established that it has an autoimmune component. Whether a person actually develops psoriasis is hypothesized to depend on something "triggering" its appearance. Examples of potential "trigger factors" include systemic infections, injury to the skin (the Koebner phenomenon), vaccinations, certain medications, and intramuscular injections or oral steroid medications.

The chronic skin inflammation of psoriasis is associated with hyperplastic epidermal keratinocytes and infiltrating mononuclear cells, including CD4+ memory T cells, neutrophils and macrophages. Because of this highly mixed inflammatory picture and the resulting complex interrelationships between these different cells, it has been very difficult to dissect the mechanisms that underlie the induction and progression of the disease.

Research into the pathogenesis and treatment of psoriasis has long been hindered by the lack of suitable animal models. Although several rodent models of skin inflammation have been recently introduced, none of these models have the specific T cell abnormalities that have been demonstrated as a primary cause for the induction of disease. The development of improved animal models having the clinical features associated with human psoriasis would be of great benefit for screening potential therapies and drugs.

2. Relevant Literature

Schon et al. (1997) *Nat. Med.* 3:183-8 induced a murine psoriasis-like disorder by reconstituting scid/scid mice with naive $CD4^+$ T cells. This model, however, lacked certain distinctive histological hallmarks of the human disease and included some characteristics that are absent from human patients with psoriasis, Nickoloff et al. (1997) *Nat. Med.* 3:475-6. Other mouse models for psoriasis have also utilized immunodeficient animals. Sugai et al. (1998) *J Dermatol Sci* 17:85-92 transplanted human psoriatic lesions onto SCID mice. The human skin grafts were generally well maintained during this period, but the histological and immunohistochemical findings characteristic of psoriasis, except for acanthosis and hyperkeratosis, gradually disappeared as lymphocytic infiltration of the psoriatic lesions declined. Yamamoto et al. (1998) *J Dermatol Sci* 17:8-14 injected staphylococcal enterotoxin B-stimulated lymphocytes subcutaneously under full-thickness psoriatic skin grafted onto severe combined immunodeficient (SCID) mice.

Gottlieb et al. (1-995) *Nat. Med.* 1:442-7-treated patients with fragments of diphtheria toxin linked to human interleukin-2 (DAB389IL-2), which selectively targets activated T cells but not keratinocytes. They showed significant clinical improvement, indicating that T cells and not keratinocytes are the primary pathogenic component in the disease.

Sundberg et al. (1997) Pathobiology 65(5):271-86 describe the development and progression of psoriasiform dermatitis and systemic lesions in the flaky skin (fsn) mouse mutant. Flaky skin (fsn) mutant mice were originally described as a mouse model for psoriasis accompanied by hematological abnormalities. However, homozygous (fsn/fsn) mice develop a number of other pathological changes.

Hong et al. (1999) J. Immunol. 162:7480-7491 (which is herein incorporated by reference for all purposes) describe improved animal models of psoriasis.

SUMMARY OF THE INVENTION

Non-human animal models are provided for psoriasis. The animals develop a disease having many of the characteristics of human psoriasis. The animals are useful for testing and screening for biologically active agents for the treatment of psoriasis. Naive, immunocompetent T lymphocytes are transferred into an immunodeficient animal host, along with at least one pro-inflammatory cytokine and a polyclonal activating agent. The engrafted T cells are tolerant to the major histocompatibility antigens of the host animal, but are mismatched at one or more minor histocompatibility loci. The engrafted animals develop a chronic skin disorder that includes histological features observed in human psoriasis, e.g. rete pegs, severe acanthosis and infiltration of Th1 cells into the dermis. These animals provide a useful model for the specific pathogenic requirements of Th1 promoting cytokines and cells for the development of psoriasiform lesions, and into the prevention and treatment of psoriasis in humans.

In another embodiment, the animal model has been used to discover a treatment for psoriasis comprising administration to patients of monoclonal antibodies that bind to and neutralize interleukin 12 (IL-12) or gamma-interferon (γ-IFN).

BRIEF DESCRIPTION OF THE DRAWINGS

FIG. 2 is a graph depicting the disease severity from weeks 14 to 18, as measured by average ear thickness, of psoriatic mice treated with anti-IL-12 antibody compared to mice treated with an isotype-matched control antibody (Isotype).

DESCRIPTION OF THE SPECIFIC EMBODIMENTS

Figure 1:
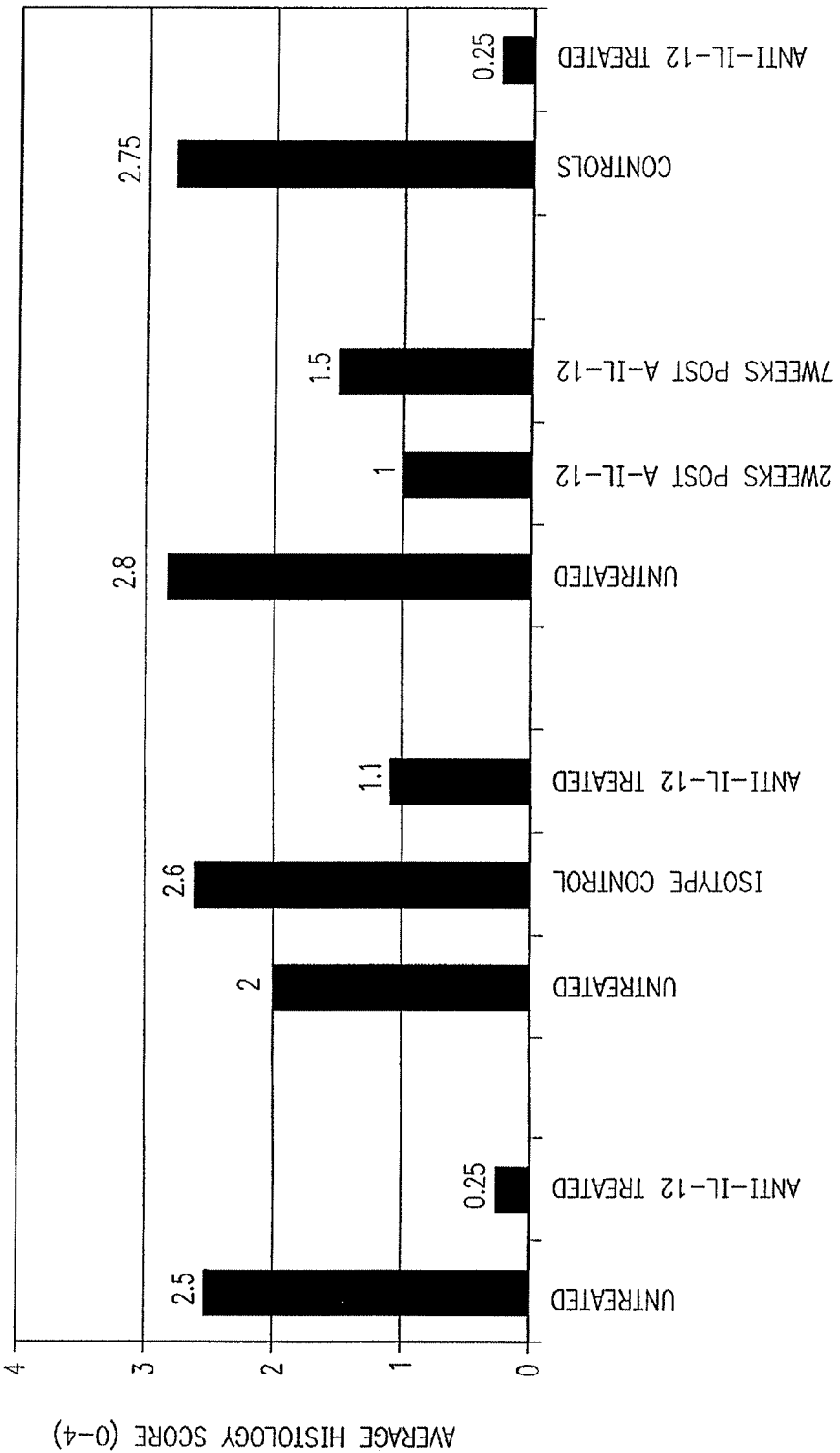
FIG. 1 is a graph depicting the results of treating psoriatic mice with antibody to IL-12. Each cluster of bars corresponds to one experiment. The average histology score represented by each bar is printed above it. α-IL-12 means anti-IL-12.

Non-human animal models having many of the histologic characteristics of human psoriasis are provided. An immunocompromised host animal is injected with a purified population of CD45Rb positive cells from a donor animal of the same or related species. Preferably, the injected cells will be CD4$^+$ CD45Rb$^{hi}$ T cells, where CD45Rb$^{hi}$ indicates that the cells are in the upper half of T cells for CD45Rb expression. The host and donor animals are tolerant of the host major histocompatibility antigens, e.g., are of the same MHC haplotype (MHC matched) but are mismatched at one or more minor antigens. The injected cells are stimulated with a pro-inflammatory cytokine, e.g. IL-12, and/or a polyclonal activating agent, before and/or after CD45Rb positive cells are transferred to the host. The animals develop a chronic skin disorder that includes histological features observed in human psoriasis, e.g. rete pegs, severe acanthosis and infiltration of Th1 cells into the dermis.

These animals provide a useful model for the specific pathogenic requirements of Th1 promoting cytokines and cells for the development of psoriasiform lesions, and into the prevention and treatment of psoriasis in humans. By providing a more accurate model for the human disease, potential therapeutics can be evaluated in the animal model for safety and efficacy prior to clinical trials. In addition to screening candidate pharmaceutical agents, the subject animals are useful in determining the role of "triggering" agents in development of the disease, the role of specific T cell subsets and cytokines, and the role of specific antigens in activation of the disease associated T cells.

Immunocompromised mammalian hosts suitable for implantation and having the desired immune incapacity exist or can be created. The significant factor is that the immunocompromised host is incapable of mounting an immune response against the introduced T cells. Of particular interest are small mammals, e.g. rabbits, gerbils, hamsters, guinea pigs, etc., particularly rodents, e.g. mouse and rat, which are immunocompromised due to a genetic defect which results in an inability to undergo germline DNA rearrangement at the loci encoding immunoglobulins and T-cell antigen receptors or to a genetic defect in thymus development (nu/nu).

Presently available hosts include mice that have been genetically engineered by transgenic disruption to lack the recombinase function associated with RAG-1 and/or RAG-2 (e.g. commercially available TIM™ RAG-2 transgenic), to lack Class I and/or Class II MHC antigens (e.g. the commercially available C1D and C2D transgenic strains), or to lack expression of the Bcl-2 proto-oncogene. Of particular interest are mice that have a homozygous mutation at the scid locus, causing a severe combined immunodeficiency which is manifested by a lack of functionally recombined immunoglobulin and T-cell receptor genes. The scid/scid mutation is available or may be bred into a number of different genetic backgrounds, e.g. CB.17, ICR (outbred), C3H, BALB/c, C57B1/6, AKR, BA, B10, 129, etc. Other mice which are useful as recipients are NOD scid/scid; SGB scid/scid, bh/bh; CB.17 scid/hr; NIH-3 bg/nu/xid and META nu/nu. Transgenic mice, rats and pigs are available which lack functional B cells and T cells due to a homozygous disruption in the CD3ε gene. Immunocompromised rats include HsdHan:RNU-mu; HsdHan:RNU-rnu/+; HsdHan:NZNU-rnu; HsdHan:NZNU-rnu/+; LEW/HanHsd-mu; LEW/HanHsd-rnu/+; WAG/HanHsd-mu and WAG/HanHsd-rnu/+.

Additional loss of immune function in the host animal may be achieved by decreasing the number of endogenous macrophages before, during, or after transfer of T cells, e.g. the reduction of macrophages by administration of dichloromethylene diphosphonate (Cl$_2$MDP) encapsulated in liposomes.

Generally, the host will be at least about four weeks old. For example, mice are often used at about 4 to 12 weeks of age. The mammalian host will be grown in conventional ways. Depending on the degree of immunocompromised status of the mammalian host, it may be protected to varying degrees from infection. An aseptic environment is indicated. Prophylactic antibiosis may be used for protection from infection. Alternatively, it may be satisfactory to isolate the potential hosts from other animals in gnotobiotic environments after cesarean derivation. The feeding and maintenance of the host will for the most part follow gnotobiotic techniques.

The major histocompatibility locus haplotype of the host animal is determined either through conventional typing methods, e.g. where outbred animals are used, or from known information concerning the genetic characteristics of the animal. In mice, the genes of the major histocompatibility locus (MHC) have been very well characterized. The MHC region is comprised of a number of genes, of which at least five contribute to acute graft rejection and graft vs. host disease. The specific MHC genes of interest include the class I antigens: H2-K, H2-D, and H2-L; and the class II antigens: H2 I region, which includes H2-Aa, Ab, Bl, Ea, Eb, Eb2, Ob, and Pb. Specific information on the haplotype of most known mouse strains may be found in Klein et al. (1983) *Immunogenetics* 17(6):553-96.

The immunocompromised host animals are injected with a purified population of CD45Rb positive T cells isolated from an immunocompetent donor. The T cells may be from an allogeneic or xenogeneic donor, and are tolerant to the major histocompatibility antigens of the recipient, but immunoreactive with one or more minor histocompatibility antigens of the recipient. By tolerant is meant that when mixed with appropriate cells (e.g., irradiated lymphocytes) from the recipient, the donor T cells proliferate to a substantially lesser extent (e.g., <about 10% to 25%) than in an analogous mixed lymphocyte reaction between MHC mismatched cells.

In contrast to the MHC locus, there are many minor histocompatibility antigen loci dispersed throughout the genome. Minor antigens generally result from the presentation of cellular proteins on the surface of cells in conjunction with self MHC. Therefore, virtually any protein that is expressed by the host, processed and presented in the context of MHC antigens, and is polymorphic between host and donor, can serve as a minor histocompatibility antigen. It has been suggested that some cutaneous antigens may serve as a trigger for psoriasis (e.g. H-40, described by Forman et al. (1984) *J. Exp. Med.* 159:1724-1740; and other antigens described by Chang et al. (1994) *P.N.A.S.* 91:9282-9286; or Menssen et al. (1995) *J. Immunol.* 155:4078-4083). The subject animals are valuable models for determining the role of specific genetic loci in contributing to the development of psoriasis. Such screening may utilize animals that are mismatched only at the loci of interest, and then determining whether the difference is sufficient for induction of disease.

There are a number of suitable animals to use as the source of T cells. In most cases the donor and recipient will be of the same species, although for some purposes xenogeneic donors may be used. In one embodiment of the invention, the donor is allogeneic but is matched at the MHC locus. For example, congenic mouse and rat strains are available that are isogenic at the MHC locus, but have a different genetic background. Alternatively, a parental strain may be used as a donor, while an F1 animal acts as recipient, e.g. a BALB/c donor into a BALB/c×C57bl/6 recipient.

Alternatively, one may use a chimeric animal as the source of donor cells. For example, one can create a chimera by transferring hematopoietic stem cells (HSC) into a recipient, where the HSC are of a different genotype than the recipient. The HSC then differentiate into T cells which are "educated" in the thymus, and so are restricted to the recipient MHC type. These cells from the chimera can then be harvested and used in the subject methods, because they are both tolerant and restricted to the MHC type of the thymus. It will be understood by one of skill in the art that the thymic MHC in this example must be compatible with the ultimate recipient animal. This procedure can also be used to create xenogeneic chimeras (see for example, U.S. Pat. No. 5,625,127), allowing the use of human cells in the subject methods.

The injected cell population comprises naive, immunocompetent T cells. A convenient marker for this population is CD45Rb, which is highly expressed in naive T cells and B cells (Serra-Pages et al. (1993) Tissue Antigens 42:441). A further separation may be obtained by sorting for CD4 positive cells, which enriches for T helper cells. Preferably, the injected cells will be $CD4^+$ $CD45Rb^{hi}$ T cells, where $CD45Rb^{hi}$ indicates that the cells are in the upper half of T cells for CD45Rb expression.

T cells are conveniently isolated from secondary immune organs, e.g. spleen, lymph node, thymus, etc. Cells may also be isolated from peripheral blood, cord blood, aphoresis product, etc. For isolation of cells from tissue, an appropriate solution may be used to disperse the spleen, lymph nodes, etc. Such solution will generally be a balanced salt solution, conveniently supplemented with fetal calf serum or other naturally occurring factors, in conjunction with an acceptable buffer at low concentration, generally from 5-25 mM. Convenient buffers include HEPES, phosphate buffers, lactate buffers, etc. Otherwise lymphocytes may be released from the tissue in accordance with conventional methods.

Separation of the desired cells for engraftment will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, LDS). Any technique may be employed which is not unduly detrimental to the viability of the selected cells.

The affinity reagents may be specific receptors or ligands for the cell surface molecules indicated above. In addition to antibody reagents, peptide-MHC antigen and T cell receptor pairs may be used; peptide ligands and receptor; ligand and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding agents are well-known to those skilled in the art.

Of particular interest is the use of antibodies as affinity reagents. Conveniently, these antibodies are conjugated with a label for use in separation or used in conjunction with a labeled second antibody that binds to them. Labels include magnetic beads, which allow for direct separation; biotin, which can be bound to avidin or streptavidin bound to a support; fluorochromes, which can be used with a fluorescence activated cell sorter; or the like, to allow for ease of separation of the particular cell type. Fluorochromes that find use include phycobiliproteins, e.g. phycoerythrin and allophycocyanins, fluorescein and Texas red.

The antibodies are added to a suspension of lymphocytes, and incubated for a period of time sufficient to bind the available cell surface antigens. The incubation will usually be at least about 5 minutes and usually less than about 30 minutes. It is desirable to have a sufficient concentration of antibodies in the reaction mixture so that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbecco's Modified Eagle Medium (DMEM), Hank's Basic Salt Solution (HBSS), Dulbecco's phosphate buffered saline (DPBS), RPMI, Iscove's medium, PBS with 5 mM EDTA, etc., frequently supplemented with fetal calf serum, BSA, HSA, etc.

The labeled cells are then separated as to the expression of CD45Rb and CD4. The separated cells may be collected in any appropriate medium that maintains the viability of the cells, usually having a cushion of serum at the bottom of the collection tube. Various media are commercially available and may be used according to the nature of the cells, including DMEM, HBSS, DPBS, RPMI, Iscove's medium, etc., frequently supplemented with fetal calf serum.

Compositions highly enriched for the desired T cells are achieved in this manner. The subject population will be preferably at or about 90% or more of the cell composition, and most preferably be at or about 95% or more of the cell composition. The enriched cell population may be used immediately, or may be frozen at liquid nitrogen temperatures and stored for long periods of time, being thawed for use when needed. The frozen cells will usually be stored in 10% DMSO, 10-90% FCS, 40% RPMI 1640 or other medium. Once thawed, the cells may optionally be expanded by use of growth factors or stromal cells associated with T cell proliferation and differentiation.

The population of purified T cells are injected into the immunocompromised recipient. Routes of administration include systemic injection, e.g. intravascular, subcutaneous, or intraperitoneal injection. Where the recipient animal is a mouse, the number of cells injected will usually be at least about $1 \times 10^5$ and not more than about $1 \times 10^6$ more usually at least about $2 \times 10^5$, preferably between about $3 \times 10^5$ and $4 \times 10^5$. Where the recipient animal is a larger animal, the number of cells will be increased accordingly.

Prior to injection, concurrently with injection of cells, and/or following injection, the T cells are stimulated with a polyclonal activating agent and/or at least one pro-inflammatory cytokine. In a preferred embodiment of the invention, the stimulation comprises injection into the T cell recipient animal of both a polyclonal activating agent and a pro-inflammatory cytokine. Administration of either or both agents is by any convenient method, e.g. systemic injection, which may be intravascular, subcutaneous, intraperitoneal, etc.; patches or implants; by inhalation, etc. Usually such stimulus is administered within about 1 day after the cells are injected, and an optional follow-up dose of the cytokine may be given within about 3 days. While some aspects of psoriasis are induced by cells alone, the severity of disease is greatly enhanced by administration of this immune stimulus.

Suitable pro-inflammatory cytokines include IL-12, IL-2, IL-15, IL-18, TNFα, IL-1α, IL-6, VEGF, and GM-CSF. Preferably the cytokine will have the same species of origin as the T cells, although some cytokines have sufficient cross-reactivity that the protein from one species will broadly stimulate cells from other species.

Of particular interest is IL-12. A preferred dose of IL-12 is at least about 0.5 ng/gram weight of recipient, and not more than about 2 ng/gram weight of recipient. IL-12 and its biological activity is described in Trinchieri (1998) *Int Rev Immunol.* 16(3-4):365-96; Gately et al. (1998) *Annu Rev Immunol.* 16:495-521. The cDNA cloning of IL-12 is described in Wolf et al. (1991) *J. Immun.* 146:3074-3081. Also of interest is the use of IL-18, which is described by Okamura et al. (1995) *Nature* 378:88-91. The cytokines can readily be produced in recombinant form by expressing the appropriate nucleic acid sequences, which are available in public databases, e.g. mouse IL-18 sequence may be found at Genbank accession number D49949. Dosage ranges for cytokines are readily determined using standard practice, e.g. dosing in 10-fold increments to determine effective ranges.

In a preferred embodiment of the invention, the pro-inflammatory cytokines are administered in conjunction with a polyclonal activating agent. Polyclonal activating agents of interest include endotoxins, e.g. lipopolysaccharide (LPS); and superantigens (exotoxins) (see Herman et al. (1991) *Annu Rev Immunol* 9:745-72). Endotoxin primarily interacts with CD14 receptors on macrophages, while superantigens preferentially activate T cells. Both cell types are thus triggered to release pro-inflammatory cytokines. Superantigens (SAgs) are presented by major histocompatibility complex (MHC) class II molecules and interact with a large number of T cells expressing specific T cell receptor V beta domains. SAgs may be endogenous, e.g. MIs; bacterial, e.g. SEB, SEA; or viral, e.g. mouse mammary tumor virus. It is of interest that bacterial infection may provide a trigger for induction of psoriasis in patients. The choice of polyclonal activating agent provides a means of assessing the potency of different superantigens and mitogens on development of the disease in the subject animal model.

The polyclonal activating agent is administered at a dose that is sufficient to activate the injected T cells, but which is below the dose at which there is observed to be systemic toxicity. The appropriate dose for different agents is readily determined by one of skill in the art. For example, with LPS the dose is usually at least about 0.1 µg/g weight of recipient and not more than about 5 g/g weight of recipient, preferably about 1 µg/g weight. A similar range of doses is used for bacterial superantigens, such as SEA and SEB.

After administration of the T cells, cytokine(s) and polyclonal activating agent, within about 4 weeks the animals develop a disease that closely mimics human psoriasis. Scoring of the disease severity is based on physical appearance and ear thickness. Symptoms include erythema on one or more locations, generally first appearing on the ears and face; and scaling over the body surface. Severe scaling is defined as covering more than about 20% of the surface of the animal. Measurement of ear thickness is conventional, using a micrometer, etc.

A more detailed analysis may utilize histological section of various tissues, conveniently ear, eyelid, tail, etc. Specific histological features include acanthosis; mononuclear cell infiltration, thickening of epidermis; high vascular density; rete pegs; hyperplasia of epidermis and keratinocytes; microabscesses; thinning of the granular cell layer; pustule formation; and destruction of granular cell layers. Such features are well described in the literature, for examples see Carroll et al. (1995) *Cell* 83:957-968; Sundberg et al. (1997) *Pathobiology* 65:271-286; and Wrone-Smith and Nickoloff (1996) *J. Clin. Invest.* 98:1878-1887.

To more fully characterize the lesions, immunophenotypic analysis may be performed to detect a variety of relevant antigenic determinants. The extent of keratinocyte proliferation may be assessed by immunostaining to detect proliferating cell nuclear antigen (PCNA). Other indicators of keratinocyte activation include HLA-DR, integrin, keratin 16, and involucrin expression. To characterize the types of immune cells present, immunohistochemical stains for various leukocyte markers may be performed. The expression of additional adhesion molecules that are relevant to the pathophysiology of psoriasis may include T cells within the epidermis and dermis; and the expression in adjacent blood vessels of focal E-selectin, and diffuse vascular cell adhesion molecule-1 (VCAM-1) expression.

A distinctive feature of the human disease, which may also be found in the animals of the invention, is the abnormal presence of rete pegs. In the epidermis, the interface with the dermis is uneven. The epidermal papillae or rete pegs are ridges and grooves that are matched by a corresponding connective tissue pattern of the dermis, called dermal papillae (this makes up the papillary layer of the dermis). These projections of epidermis created by dermal papillae appear as columns of cells in section.

Drug Screening Assays

In addition to assessment of the role in disease induction of various components, e.g. minor histocompatibility antigens; T cell sub-populations; pro-inflammatory cytokines; and polyclonal triggers; the subject animals are useful for screening candidate therapeutic agents and treatment modalities. Through use of the subject animals or cells derived therefrom, one can identify ligands or substrates that affect the progression of psoriasis. Of particular interest are screening assays for agents that have a low toxicity for human cells.

A wide variety of assays may be used for this purpose, including histological analysis of effectiveness, determination of the localization of drugs after administration, labeled in vitro protein-protein binding assays, protein-DNA binding assays, electrophoretic mobility shift assays, immunoassays for protein binding, and the like. Depending on the particular assay, whole animals may be used, or cells derived therefrom, particularly skin cells, e.g. keratinocytes. Cells may be freshly isolated from an animal, or may be immortalized in culture. Candidate therapies may be novel, or modifications of existing treatment options. Currently available treatment for psoriasis includes:

TABLE 1

| THERAPY | NOTES |
|---|---|
| Antibiotics, antimicrobials | Infections may worsen (flare) psoriasis |
| Cyclosporine | Suppresses the body's immune system; use for more than one year not recommended |
| Methotrexate | Effective in psoriasis and psoriatic arthritis; Lifetime cumulative dose of 4.5 grams has been associated with up to 25% risk of liver/cirrhosis/fibrosis |
| Hydroxyurea, NSAIDS, Sulfasalazine, 6-thioguanine | |
| Retinoids—acitretin, etretinate, isotretinoin | Etretinate, labeled for psoriasis, has been replaced by acitretin |
| ULTRAVIOLET LIGHT | |
| Hospitalization, Outpatient day treatment | For severe psoriasis: Intensive nurse administered therapy of day-long UV and prescription topicals for 30 days or more |
| Phototherapy (UVB) | Minimum 20-40 treatments to clear psoriasis; additional treatments may prolong clearance |
| Photochemotherapy (PUVA) | Combines ingestion, soaking, or painting with psoralen medication before exposure to UVA light. Minimum 20 treatments to produce substantial clearing; additional to prolong clearance |
| Home phototherapy (UVB) | Durable medical equipment for home use to prolong clearance in physician-selected patients. |
| TOPICAL AND INTRALESIONAL THERAPY | |
| Anthralin | Compounded in various strengths, can be combined with UV exposure |
| Calcipotriene | Topical vitamin D is first in this class to be approved for psoriasis |
| Coal Tar | Compounded in various strengths, can be combined with UV exposure |
| Corticosteroids—low strength | Applied to skin |
| Corticosteroids—moderate to potent | Various potencies, applied to skin, injected into lesions, or taken orally |
| Emollients | Preserves skin flexibility |
| Keratolytics—salicylic acid | Compounded in various strengths, used with tar or emollients |
| Tazarotene | First topical vitamin A derivative approved for psoriasis |

For screening assays that use whole animals, a candidate agent or treatment is applied to the subject animals. Typically, a group of animals is used as a negative, untreated or placebo-treated control, and a test group is treated with the candidate therapy. Generally a plurality of assays are run in parallel with different agent dose levels to obtain a differential response to the various dosages. The dosages and routes of administration are determined by the specific compound or treatment to be tested, and will depend on the specific formulation, stability of the candidate agent, response of the animal, etc.

The analysis may be directed towards determining effectiveness in prevention of disease induction, where the treatment is administered before induction of the disease, i.e. prior to injection of the T cells and/or pro-inflammatory cytokine. Alternatively, the analysis is directed toward regression of existing lesions, and the treatment is administered after initial onset of the disease. Frequently, treatment effective for prevention is also effective in regressing the disease.

In either case, after a period of time sufficient for the development or regression of the disease, the animals are assessed for impact of the treatment, by visual, histological, immunohistological, and other assays suitable for determining effectiveness of the treatment. The results may be expressed on a semi-quantitative or quantitative scale in order to provide a basis for statistical analysis of the results.

The term "agent" as used herein describes any molecule, e.g. protein or pharmaceutical, with the capability of affecting the severity of psoriasis. An agent or treatment, e.g. UV light, is administered to an animal of the invention, or to cells derived therefrom. Antibodies specific for cytokines, polyclonal activating agents, and T cell antigens are agents of particular interest. Most preferably, according to another aspect of the instant invention, the agents are monoclonal antibodies, e.g. which neutralize lymphokines or block adhesion molecules.

By way of example but not limitation, the antibodies may be specific for IL-12, or γ-IFN. Exemplary antibodies include HuZAF, a humanized anti-IFN-γ antibody (described in commonly assigned U.S. provisional patent application No. 60/110,523, filed Dec. 1, 1998); HuEP5C7, a humanized anti-E/P selectin antibody (described in U.S. Pat. No. 5,622, 701); and HuM291, a humanized anti-CD3 antibody (described in PCT publication WO 96/26964).

Other candidate agents encompass numerous chemical classes, typically organic molecules. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The therapeutic agents may be administered to patients in a variety of ways, orally, topically, parenterally e.g. subcutaneously, intramuscularly, intravascularly, etc. Depending upon the manner of introduction, the compounds may be formulated in a variety of ways. The concentration of therapeutically active agent in the formulated pharmaceutical compositions may vary from about 0.1-100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Therapy with Antibodies that Neutralize IL-12 or Gamma Interferon

In other embodiments of the present invention, agents that block the effects of the lymphokines interleukin 12 (IL-12) or gamma interferon (IFN-γ) are used to treat a patient with psoriasis. These agents may be small molecules as described above, but are preferably proteins. In preferred embodiments, the agent is an antibody, especially a monoclonal antibody, that binds IL-12 or IFN-γ. The monoclonal antibody may be derived from any convenient species, e.g., mouse, rat, hamster, etc. by methods well known in the art (see, generally, Harlow & Lane, Antibodies, A Laboratory Manual, Cold Spring Harbor Press, NY, 1988). Preferably, the antibody will be chimeric (see, e.g., Cabilly et al., U.S. Pat. No. 4,816,567 which is herein b incorporated by reference for all purposes) or humanized, i.e., formed by linking the complementary determining regions (CDRs) of a non-human antibody to an essentially human framework and constant region by recombinant DNA techniques (see, e.g., Queen et al., U.S. Pat. No. 5,585,089, which is herein incorporated by reference for all purposes). Alternatively, the antibody may be human, as made, e.g., by trioma technology (see, e.g., U.S. Pat. No. 4,634,664) or from transgenic animals (see, e.g., Lonberg et al., WO 93/12227 and Kucherlapati, WO 91/10741, each of which is herein incorporated by reference for all purposes) or by phage display methods (see, e.g., Dower et al., WO 91/17271 and McCafferty et al., WO 92/01047, and Winter WO 92/20791, each of which is herein incorporated by reference for all purposes).

Preferably, the monoclonal antibody will have binding affinity (association constant) for its antigen of at least $10^8$ $M^{-1}$ or more preferably $10^9$ $M^{-1}$ or higher. Most preferably, the antibody will neutralize IL-12 or IFN-γ, that is block one or more of its biological functions, for example the ability to bind to its cellular receptor. Other functions that may be blocked by a neutralizing antibody are exemplified for IFN-γ in commonly assigned U.S. provisional patent application No. 60/110,523 and for IL-12 in Gately et al., U.S. Pat. No. 5,780,597 and Gately et al. WO 99/37682 (each of which is herein incorporated by reference for all purposes), e.g., blocking the IFN-γ inducing function of IL-12. Preferably, a concentration of 0.001, 0.005, 0.01, 0.05, 0.1, 0.25, 0.5, 1, 2, 5, or 10 µg/ml of the antibody will block 25%, 50%, 90%, 95%, 99% or essentially 100% of the function of the respective lymphokine, especially when the lymphokine is also used at one of these concentrations or at a molar concentration that is 0.005, 0.01, 0.05, 0.1, 0.25, 0.5 or 1.0 of the concentration of the antibody. Exemplary IFN-γ neutralizing antibodies are HuZAF or other humanized forms of AF2 (as described in U.S. provisional patent application No. 60/110,523). Exemplary IL-12 neutralizing antibodies are 5F2, 16F2, 16G2, and 20E11 (as described in Gately et al. WO 99/37682) and their chimeric and humanized forms. Other preferred antibodies have the same or overlapping epitopes as the aforementioned antibodies, that is they compete (cross-block) with them for binding to antigen, or in which some of the same amino acids of the antigen are shown by in vitro mutagenesis to contribute to binding. Particularly preferred anti-IL-12 antibodies will bind to the p75 IL-12 heterodimer but not to the individual subunits such as p40.

Alternatively, instead of an antibody, an extracellular portion of a cellular receptor (or its binding subunit) for IL-12 or IFN-γ can be recombinantly linked to the Fc region of a human immunoglobulin (e.g., IgG1) to improve its half-life or other properties. See, e.g., Ashkenazi et al. (1991), Proc. Natl. Acad. Sci. USA 88:10535-9 and Moosmayer et al. (1995), J. Interferon Cytokine Res. 15:1111-5 (each of which is herein incorporated by reference for all purposes) for methods of constructing such fusion proteins ("immunoadhesins"). Receptors for IL-12 and IFN-γ are respectively described in Chua et al. (1994), J. Immunol. 153:128-36 and Presky et al. (1996), Proc. Natl. Acad. Sci. USA 93:14002-7; and Aguet et al. (1988), Cell 55:273-80 (each of which is herein incorporated by reference for all purposes). The fusion protein will bind to and neutralize IL-12 or IFN-γ respectively and will have properties similar to an antibody and may therefore be used for the treatment of psoriasis. In what follows, the term "antibody" will be understood to also encompass fusion proteins of this type.

For administration to patients, the antibody (or fusion protein) drug will typically be formulated in a pharmaceutically acceptable carrier. A variety of aqueous carriers can be used, e.g., water for injection (WFI), or water buffered with phosphate, citrate, acetate, etc. to a pH typically of 5.0 to 8.0, most often 6.0 to 7.0, and/or containing salts such as sodium chloride, potassium chloride, etc. to make isotonic. The carrier may also contain excipients such as human serum albumin, polysorbate 80, sugars or amino acids such as arginine, histidine or glycine to protect the active protein. The concentration of antibody in these formulations may vary widely from about 0.01 to 100 mg/ml but will most often be in the range 1 to 10 mg/ml. The formulated antibody is particularly suitable for parenteral administration, and may be administered as an intravenous infusion or by subcutaneous, intramuscular or intravenous injection, and may also be administered by injection at the site of disease, e.g., into the psoriatic lesions.

Doses of the drug will typically contain from 0.01 to 100 mg antibody (or fusion protein) but most often from 0.1 to 1, or 1, 2 or 5 to 10 mg per kilogram body weight or as a unit dose, in an amount sufficient to alleviate the disease without causing unacceptable side effects ("therapeutically effective dose"). The antibody drug may be administered once or multiple times, e.g., 1, 2 or 3 times per day, week or month for one to several days, weeks, months or years, or chronically, depending upon the nature and severity of the disease. The antibody will often be administered after or in combination with one or more other immunosuppressive drugs or other therapies, for example, corticosteroids, cyclosporine, methotrexate, phototherapy (with or without PUVA) or others listed in Table 1 above. The anti-IL-12 or anti-IFN-γ antibody may also be used together or in combination with other antibodies, for example to adhesion molecules or lymphokines such as CD11a, CD40 ligand, IL-8 or to their receptors (e.g., IL-2 receptor).

The severity of psoriasis is measured by the Psoriasis Area Severity Index (PASI) (see e.g., Fleischer et al. (1999), J. Dermatol. 26:210-215 and Tanew et al. (1999), Arch Dermatol. 135:519-524) or various psoriasis global assessment scores such as Physician's Global Assessment (PGA) which are well-known to those skilled in the art of clinical trials for psoriasis. Treatment with the (e.g., humanized or human) antibody to IL-12 or IFN-γ will reduce the PASI (or global assessment score) by at least 25% or 40% but preferably 50% or even 60 or 70% or more in at least 50% but preferably 60-70% or 75% or more of the patients treated. Alternatively, such treatment will cause a greater reduction in a smaller group or patients, i.e., at least 75% but preferably 80-90% or more or even essentially complete clearance, in at least 20% to 25% but preferably 30% to 40% or even 50% or more of the patients. This reduction will typically last at least 2 but preferably 3 or more months, or even 4 to 6 or more months, but most preferably a year or longer, either while treatment with the antibody is continued or after it is stopped. Typically, in a clinical trial (e.g., a phase II or phase III trial), the improvement in PASI or score in the patients treated with the anti-IL-12 or anti-IFN-γ antibody, relative to the control group of patients receiving no treatment or placebo or another agent, will be statistically significant, for example at the p=0.05 or 0.01 or even 0.001 level.

Alternatively, the antibody to IL-12 or IFN-γ can be administered after remission has already been induced by another drug, for example corticosteroids, cyclosporine, methotrexate, phototherapy (with or without PUVA) or others listed in Table 1 above. In this case, treatment with the antibody will increase the median time to relapse (e.g., 50% worsening in PASI) by at least 40% but preferably 50% and most preferably 60-70% or more or even 100% (doubling) or more. Typically, in a clinical trial (e.g., a phase II or phase III trial), this increase of time to relapse in the patients treated with the anti-IL-12 or anti-IFN-γ antibody, relative to the control group of patients receiving no treatment or placebo or another agent, will be statistically significant, for example at the p=0.05 or 0.01 or even 0.001 level.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which scope will be determined by the language in the claims.

It must be noted that as used herein and in the appended claims, the singular forms "a", "and", and "the" include plural referents unless the context clearly dictates otherwise. Thus, for example, reference to "a mouse" includes a plurality of such mice and reference to "the cytokine" includes reference to one or more cytokines and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for all relevant purposes, e.g., the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Materials and Methods

Mice.

Female BALB/cj mice and BALB/cj-IFNγ$^{-/-}$ mice (donor mice) were purchased from Jackson Labs (Bar Harbor, Me.). C.B-17/lcr scid/scid mice and C.B-17 scid-beige double mutant mice (recipient mice) were purchased from Taconic (Germantown, N.Y.). All mice were housed in a specific pathogen free environment at the Protein Design Labs animal facility and were used between 4-12 weeks of age. Sentinel mice were used to screen for the following pathogens: MHV, sendai, PVM, REO3, TMEV GDVIII, *M. pulmonis* and parvovirus. Random screens of mice for pinworms were also conducted. None of the pathogens listed above were detected at anytime. Mice were housed 2-5 per microisolator. All scid/scid or scid/beige mice were handled with gloves under a class II hood, fed sterile food and water ad libitum, and maintained inside a laminar flow tent (Bioclean Maywood, N.J.) in sterile microisolators that were changed weekly. Donor mice were housed in conventional cages that were changed weekly.

Cell Purification, and Injection into scid/scid Mice.

Spleens were collected from 6-12 week old donor mice (BALB/cj or IFNγ$^{-/-}$-BALB/cj) and splenocytes were isolated by mechanical homogenization of whole spleens. CD4+ T cells were selected by positive selection. In brief, a cell suspension of pooled splenocytes from 4-5 donor mice was incubated with anti-CD4 (L3T4) antibody coated magnetic beads (DYNABEADS: Catalog #114.05, Dynal, Lake Success, N.Y.) for 20-30 minutes at 4° C. and separated by magnetic cell sorting with a Dynal Magnetic Particle Concentrator (MPC). Cells were removed from the cell-bead complex with Dynal DETACHaBEAD, and isolated from beads using a Dynal MPC. The resulting CD4+ enriched population was >90% pure. The cell suspension ($10\times10^6$ cells/ml) was then incubated with Fc block (anti-CD32, PharMingen, 01241A) (10 g/ml) and labeled with anti-CD4-FITC (PharMingen, 9004D) and anti-CD45RB-PE (PharMingen, 01145A) (both at 10 µg/ml), for 30 minutes at 4° C., washed, and sorted using a FACSTAR (Becton Dickinson, San Jose, Calif.) cell sorter. Double positive cells (CD4+/CD45Rb+) were collected, selecting the cells that expressed high levels of CD45Rb (brightest 45%). The collected cell population was >90% pure and viable. Cells were then washed in cold potassium buffered saline (PBS Sigma D8662) and resuspended in PBS at $1.5\times10^6$ cells/mL. C.B-17/lcr scid/scid mice, aged 4-6 weeks, were injected intravenously with $3\times10^5$ cells each, 200 µL total volume into the tail vein.

Induction and Treatment of Psoriasiform Lesions in scid Mice.

To study the effect of microbial products and IL-12, recipient mice were treated as follows: A control group received CD4+ CD45Rb$^{hi}$ sorted cells with no additional treatment. A second group was given 20 µg lipopolysaccharide (LPS) from *Salmonella enteritidis* (Sigma L-2012) i.p. per mouse on day 1 after cell transfer. A third group received 10 ng IL-12 (Pharmingen, Calif.) alone per mouse delivered i.p. on days 1 and 3. The final group was injected i.p. with a combination of LPS and IL-12. Dosage studies were conducted using 2, 10, and 100 ng doses of IL-12 in conjunction with 20 µg LPS. The LPS and IL-12 injection was given on day 1 following T cell transfer and an additional dose of IL-12 was administered on day 3. In additional studies, LPS (20 g) and IL-12 (10 ng) were administered once weekly for 3 weeks. Some experimental groups received 10 g Staphylococcal enterotoxin B protein from *Staphylococcus aureus* (Sigma catalog S4881) i.p. per mouse once on day 1 following T cell transfer.

To study the role of IFNγ, T cells from BALB/c-IFNγ$^{-/-}$ mice (Jackson labs) T cells were isolated by the same methods described above. Recipient scid/scid mice were also co-injected with 20 µg LPS and 10 ng IL-12 on day 1 and 10 ng of IL-12 on day 3. In addition, scid-beige mice (Taconic), that are T-, B- and NK-cell deficient, were used as recipient mice for IFNγ$^{-/-}$ T cell transfer in some experiments. For interventional studies, 0.5 mg anti-IL-12 (clone C17.8, PharMingen, San Diego, Calif.) was given i.p. to mice on day 7 and 35. Control mice received either PBS or rat IgG (Sigma) on the same day.

Clinical Evaluation.

Mice were evaluated by three different investigators at weekly intervals commencing on week 4 and ending on week 10. To record disease progression semi-quantitative clinical scores from 0 to 4 were given based on physical appearance and ear thickness. 0=no skin or ear symptoms; 1=mild, moderate erythema on ears or eyelids with mild thickening of the ear; (<2% of the body surface) 2=moderate to severe erythema on one location (mostly ear and face) (2-10% of the body surface), mild scaling; 3=severe erythema at two or more sites (ear, face, trunk) (>10% of the body surface), severe scaling; 4=very severe, extensive erythema throughout the body (>20% of the body surface) with severe scaling.

Specific observations were noted based on fur condition, ear manifestations, eyelid appearance, presence of inflammation on limbs and tail. Ear thickness was determined using a modified spring micrometer (Oditest; Dyer, Inc). Measurements were taken from the same part of the ear for all data time points from =both the right and left ear. The micrometer was allowed to settle while on the ear to prevent tissue edema from affecting final measurement.

Histopathologic Analysis and Immunohistology of Skin Tissue Samples.

Necropsies were performed on mice at week 10-12 after cell transfer. Tissue no samples from ear, eyelid and tail were collected and fixed in paraformaldehyde solution and submitted to Comparative Bioscience (Sunnyvale, Calif.) for section preparation and analysis. To record disease severity, semi-quantitative histological scores from 0 to 4 were given based on the severity of inflammation. Initial histological evaluation was performed by an independent outside pathologist. In later studies evaluation was blindly conducted by three different investigators. Mice which had ear thickness of 25 µm or less with no additional clinical signs were automatically given a histology score of zero without section analysis. 0=no signs of inflammation; 1=very low focal areas of infiltration, mild acanthosis; 2=low level of mononuclear cell infiltration, mild thickening of epidermis, mild to moderate acanthosis 3=high level of mononuclear cell infiltration, high vascular density, thickening of the epidermis (acanthosis, rete pegs and hyperplasia of epidermis and keratinocytes, microabscesses, thinning of the granular cell layer 4=very extensive infiltration in epidermis and dermis, very high vascular density, extreme thickening of epidermis, pustule formation and destruction of granular cell layers.

Tissue samples were collected and embedded in Tissue Tek OCT compound and frozen with dry ice for cryostat-cut sections. Tissue sections (5 µm) were fixed in 100% acetone and stained with PE-conjugated IL-12 mAb (p40/70) (Pharmingen, clone C17.8). Tissues were evaluated as positive or negative based on visual fluorescent microscopy detection.

Skin Infiltrating Lymphocyte Cell Isolation.

Skin infiltrating lymphocytes (SIL) were isolated via enzyme digestion. In short, skin, ears, and eyelids were minced with sterile scissors, and the pieces washed with HBSS over a 100 mm nylon cell strainer (Falcon) to remove surface debris. Infiltrating cells were liberated by incubating the cut pieces in 25 mL of warm (37° C.) HBSS media without Ca/Mg (BioWhittaker, Walkersville, Md. 10-543F) supplemented with 25 mM HEPES buffer (BioWhittaker 17-737E) and 10% FCS (HyClone Labs Inc., Logan, Utah SH30071.03) for 20 min at 37° C. The remaining pieces were washed over nylon mesh, resuspended in RPMI 1640 media (BioWhittaker 12-702F) augmented with 25 mM HEPES buffer, 10% FCS, 400 U/mL DNAse (Boehringer Mannheim Biochemicals, Indianapolis, Ind. 104159), 400 U/mL collagenase (Boehringer Mannheim 1088874), and incubated 90 minutes at 37° C. on a rocker. The resulting cell suspension was filtered sequentially through a 100 µm and 40 µm nylon mesh filter and then washed twice in RPMI 1640 supplemented with 25 mM HEPES and 10% FCS.

In vitro stimulation of SIL and detection of cytokines. SIL were resuspended at $10^6$/mL in complete media RPMI 1640 supplemented with 10% FBS (HyClone), $5\times10^{-5}$ M 2-mercaptoethanol (Sigma), 2 mM glutamine (Life Technologies), 10 U/mL penicillin/100 µg streptomycin (Life Technologies) and 15 mM HEPES. CD4+ sorted T cells were resuspended at $2.5\times10^5$/mL. 2001 per well of this suspension was then placed in a 96 well tissue culture plate (Falcon 3072) and incubated for 48 hours with αCD3 (PDL, clone 145-2C11) and αCD28

(PharMingen), each at 1 µg/ml. Supernatants from three different culture wells were collected and tested by ELISA for IFNγ, TNFα, and IL-4. The ELISA procedure involved coating a 96 well flat bottom Immulon 4 plate (Dynatech Labs, Inc 011-010-3850) overnight at 4° C. with 50 µl of a 2 g/mL solution of anti-IFNγ, anti-TNFα or anti-IL-4 antibody (all from Pharmingen) in carbonate buffer. Plates were then washed with PBS/Tween (0.05% Tween 20 in PBS) and blocked with 200 µl sterile solution of PBS with 3% BSA (Sigma bovine albumin A7030) for 1 hour at 37° C. In between all of the following steps, plates were washed with PBS/Tween. IFNγ, IL-4 and TNFα standards as well as sample supernatants were then added to wells and incubated for 2 hours at 37° C. Biotin conjugated secondary antibodies for anti-IFNγ, anti-TNFα, and anti-IL-4 (all antibodies from Pharmingen) were then added to the respective plates at 2 µg/mL in 3% BSA/PBS solution and incubated for 1 hour at 37° C. Horse radish peroxidase (HRP) labeled streptavidin (Jackson ImmunoResearch Labs 016-030-084) was then added at a concentration of 1 µg/mL. O-Phenylenediamine (Sigma 4664) was then used as substrate buffer per manufacturer's protocol. Assay was then read on a Molecular Devices (Sunnyvale, Calif.) plate reader and data analyzed using SOFTmax™ software.

Results

Treatment of Scid/Scid Mice Restored with CD4+/CD45Rb$^{hi}$ T Cells with LPS Plus Low and Medium Doses of IL-12 Results in Increased Incidence and Severity of Psoriasis; High Doses of IL-12 Prevent Disease Induction.

Previous studies have demonstrated that scid/scid mice reconstituted with minor haplotype mismatched CD4+/CD45Rb$^{hi}$ Balb/c T cells sometimes develop chronic skin inflammation that resembles human psoriasis. In initial experiments, it was found that when BALB/c CD4+/CD45Rb$^{hi}$ T cells alone were transferred to C.B-17 scid/scid mice, only a few animals exhibited psoriasiform lesions and the expression of disease was rather mild. This finding was consistent with previous observations made by Schon et al. (1997), supra. Because bacterial mitogens or bacterial superantigens have been shown to be potent modulators of cell-mediated immune responses, and IL-12 has been demonstrated to play an important role in the induction of various autoimmune conditions, it was initially tested whether the co-administration of such agents would have an effect on the induction of psoriasis in the scid/scid transfer model. As shown in Table 2, when C.B-17 scid/scid mice were reconstituted with BALB/c CD4+/CD45Rb$^{hi}$ T cells alone, only 38% of the mice developed psoriasiform skin lesions and 27% of the mice developed severe forms of disease. When LPS was co-administered alone, we observed a slight increase in disease incidence (50%), but the severity of the lesions remained similar to lesions in mice that had received cells alone. Similarly, co-administration of a medium dose (10 ng/mouse) of IL-12 alone on day 1 and 3 following T cell transfer led to an apparent increase in disease incidence (67%) without affecting disease severity.

TABLE 2

In vivo administration of IL-12 in combination with LPS after CD4+/CD45Rb$^{hi}$ T cell transfer leads to a significant increase in disease expression.

| Post Cell Transfer Treatment[1] | Disease Incidence[2] | Average Histology Score[3] | Severe Disease[4] |
|---|---|---|---|
| PBS | 10/26 (38%) | 1.1 ± 1.4 | 7/26 (27%) |
| IL-12 medium | 2/3 (67%) | 0.75 ± 1 | 0/3 (0%) |
| LPS | 2/4 (50%) | 0.6 ± 0.7 | 0/4 (0%) |
| LPS + IL-12 low | 6/11 (55%) | 1.9 ± 1.0 | 4/11 (36%) |
| LPS + IL-12 medium | 24/33 (73%) | 2.25 ± 1.1 | 14/33 (42%) |
| LPS + IL-12 high | 0/4 (0%) | 0.0 | 0/4 (0%) |
| LPS + IL-12 medium[5] | 8/10 (80%) | 2.5 ± 1 | 5/10 (50%) |
| LPS + IL-12 medium[6] | 0/8 (0%) | ND | 0/8 (0%) |
| SEB | 3/4 (75%) | ND | 2/4 (50%) |

[1]After CD4+/CD45Rbhi cells isolated from BALB/cj spleens were transferred to scid/scid mice, the recipient mice were given the following treatments. The PBS group received sorted cells with no additional treatment. The IL-12 group received 10 ng IL-12 alone per mouse delivered i.p. on days 1 and 3 in addition to cells on day 0. The LPS group was given 20 µg Lipopolysaccharide (LPS) from *Salmonella enteritidis* (Sigma L-2012) per mouse on day 1 after cell transfer. Dosage studies were conducted using the low (2 ng), medium (10 ng), or high (100 ng) doses of IL-12 in conjunction with 20 µg LPS. The LPS and IL-12 injections were given on day 1 and an additional dose of IL-12 was administered on day 3. In a different series of experiments LPS (20 µg) and IL-12 (10 ng) were injected once a week for three weeks. Other mice received 10 µg Staphylococcal enterotoxin B protein from *Staphylococcus aureus* (Sigma catalog S4881) per mouse once on day one.
[2]Disease incidence is reported as number of mice with disease over 12 weeks of time: criteria being ear thickness ≥26 µm or clinical score of ≥1. Ear thickness of normal scid/scid mice: 21 ± 1 µm (n = 10).
[3]Histological scores of diseased mice from 1 to 4 were given based on the severity of inflammation of ear, skin or eyelid. Mice which had ear thickness of 25 µm or less were categorized as undiseased (average ear thickness of undiseased mice 22 µm ± 1) and automatically excluded from section analysis. 0 = no signs of inflammation; 1 = very low level and 2 = low level of mononuclear cell infiltration, mild thickening of epidermis; 3 = high level of mononuclear cell infiltration, high vascular density, thickening of the epidermis (acanthosis, rete pegs and hyperplasia of epidermis and keratinocytes); 4 = very extensive mononuclear cell infiltration in epidermis and dermis, very high vascular density, extreme thickening of epidermis, pustule formation and loss of granular cell layers, p versus PBS control: LPS + IL-12 low, p < 0.1, LPS + IL-12 medium, p < 0.008. Statistical analysis was performed using the two-tailed student t test.
[4]Severe disease induction calculated as the number of animals that received an average histology score of ≥2.5 and/or a clinical score of ≥3.
[5]LPS (20 µg) and IL-12 (10 ng) was given once a week for 3 weeks.
[6]3 x 10$^5$ unsorted CD4+ T cells (CD45Rb$^{hi}$ and CD45Rb$^{lo}$) were transferred into scid/scid mice. LPS (20 µg) and IL-12 (10 ng) was given once a week for 3 weeks.

In contrast, recipient mice that received either 1 or 10 ng IL-12 on day 1 and day 3 along with 20 µg of LPS on day 1 following T cell transfer showed an increase in disease severity and incidence. In particular, the administration of a medium doses of IL-12 (10 ng/mouse) along with LPS showed a 73% incidence of disease with an average histology score of the diseased mice of 2.25±1.1, which was significantly higher than when PBS was co-administered (p<0.008). In addition, the percentage of animals with severe disease in the IL-12 medium dose group was also higher (42%) when compared to the IL-12 low dose group (36%) and significantly higher when compared to the PBS control (27%). Interestingly, co-administration of LPS (20 µg/mouse) and a high dose of IL-12 (100 ng/mouse) completely inhibited disease development (incidence 0%). When LPS and medium doses of IL-12 (10 ng) were co-administered once a week for three weeks the incidence of disease was 80% (8/10) with an average clinical score of 2.5±1 (Table 2). This particular induction protocol was also associated with an accelerated onset of disease as the animals in this group came down with disease as soon as 4 weeks after T cell transfer. In contrast, animals that had received only one dose of LPS and IL-12 (10 ng) developed disease at an average of 6-8 weeks after T cell transfer, and animals that received T cells only developed signs of disease at an average of week 8 to 10 after T cell transfer.

Animals that had received unsorted CD4 T cells never came down with disease even if they were treated with three administrations of LPS (20 µg) and IL-12 (10 ng) (Table 2), indicating that LPS and IL-12 administration can only act on naïve T cells and the regulatory effects of CD45Rb$^{lo}$ cells can not be overcome by the administration of microbial factors and IL-12. Of note, mice that received no T cells or T cells alone were housed together with mice that received T cells plus LPS and IL-12, to ensure that other exogenous factors did not play a role in the induction of disease.

In a different set of experiments, we tested whether other microbial products such as SEB exert an influence on disease expression as well. As shown in Table 2, SEB was also able to induce disease at a higher incidence and severity (average clinical score 1.5±0.9) than cells alone; thus demonstrating that the ability of bacterial constituents to modulate the expression of psoriasiform lesions is not unique to LPS.

Additionally, in separate cell transfer studies, it was found that scid/scid mice that received cells isolated from the skin lesions of diseased mice did not develop psoriasis unless LPS and IL-12 was co-administered, indicating that the transfer of inflammatory psoriatic T cells alone is not sufficient to induce a chronic inflammatory response in the skin.

Psoriatic Skin Lesions of Scid/Scid Mice Treated with LPS and IL-12 Resemble Closely Human Pathology.

Animals that received $CD4^+/CD45Rb^{hi}$ cells in conjunction with LPS and IL-12 developed disease symptoms as soon as 4-8 weeks after cell transfer. Mice that showed no clinical signs of disease at week 10 post T cell transfer remained disease free for an additional 4-6 weeks of observation. Thus, mice were monitored beginning on week 4 and necropsies were performed on subject animals between week 10-12. Clinical signs of disease consistently included increased ear redness, and thickened skin on ears and eyelids. Some animals also showed signs of significant skin inflammation on the tail. In more severe cases, skin inflammation was observed throughout the body with increased scaling and hair loss (clinical score 4). Ear thickness typically varied from a base line of 21±1.1 μm in undiseased animals to a pathological range of 26 to 50 μm. Skin that became severely affected consistently became scaly, ulcerated, and typically showed plaque-type elevation. Skin inflammation in psoriatic mice ranged from mild, around the base of the ears and around the eyelids (clinical score 1-2), to severe hair loss that extended to over 75% of their body (clinical score 3-4). Since ear thickness correlated very well with the severity of disease and clinical scores, we used the measurement of ear thickness as an indicator for overall skin inflammation in most experiments.

Other psoriasis-like models in mice have been criticized for not possessing the histological characteristics found in human forms of disease. Differences in the mouse skin structures were deemed responsible for these discrepancies. An absence of rete pegs or ridge elongation in mice, a major hallmark in human disease, was attributed to the relatively flat dermoepidermal junction in mice. Histological analysis of the lesions induced by our protocol was performed by taking biopsies of skin samples from several areas of diseased mice and examining 3 μm sections stained with hematoxylin and eosin. Samples taken from the ear, eyelid and tail of diseased mice that had received T cells plus LPS (20 μg/mouse) and IL-12 (10 ng/mouse) were prepared for histologic evaluation and microscopically examined by an independent pathologist. Most lesions were found to have typical signs of parakeratosis and hyperkeratosis with some ulcer or erosion and pustule formation. Also noted was a thickening of the epidermis (acanthosis) with proliferation of the keratinocytes and moderately deep rete pegs in the subcutis; the inflammatory cell infiltration consisted of primarily mononuclear cells composed of lymphocytes with fewer monocytes, macrophages and plasma cells. Variable numbers of neutrophils with a few eosinophils were also seen. Capillaries and other vessels were numerous, contained large numbers of marginated neutrophils and were typically surrounded by lymphocytes. The combination of these characteristics indicate that the psoriasiform lesions in this model are very comparable to those found in humans. Sections from normal scid/scid mice that received no T cells were taken at the same age as diseased mice. The epidermis is 1-2 cells thick and the dermis contains almost no lymphocytes. In addition, the density of vessels is sparse. The junction of the dermis to the epidermis is straight and contains no abscesses.

CD4+ T Cells from the Skin of Mice with Psoriasis are $CD45Rb^{lo}$ and Produce High Levels of IFNγ and Low Levels of IL-4.

To compare the activation/cytokine profile of skin infiltrating lymphocytes (SIL), we purified this population from the skin lesions of diseased and undiseased mice. Isolated SIL were stimulated in vitro with anti-CD3 and anti-CD28 for 48 hrs and supernatants were tested for the production of IFNγ, TNFα and IL-4. Lymphocytes isolated from the skin of mice that received T cells but showed no clinical signs of disease did not secrete any detectable levels of IFNγ or IL-4. In contrast, cells from diseased mice expressed very high levels of IFNγ and TNFα and low levels of IL-4 (Table 3). Naïve $CD4^+/CD45Rb^{hi}$ donor cells from spleens of BALB/c were stimulated in a similar fashion and showed no detectable levels of any cytokine tested. Furthermore, the majority of CD4+ cells isolated from the inflamed tissue of diseased were $CD45Rb^{lo}$. The data suggests that the majority of naïve T cells transferred into scid/scid mice differentiate in the microenvironment of the skin into Th1-like memory/effector T cells.

TABLE 3

CD4+ T cells isolated from psoriatic lesions of scid/scid mice produce high levels of interferon-gamma and low levels of IL-4

| T cell Source | IFNγ (pg) | IL-4 (pg) | TNFα (pg) |
|---|---|---|---|
| Skin from scid/scid-diseased[1] | 22987 ± 648 | 468 ± 79 | 4654 ± 946 |
| Skin from scid/scid-undiseased[2] | ≤20 | ≤15 | ≤35 |
| CD4+/CD45RB$^{hi}$ T cells from BALB/c spleens[3] | ≤20 | ≤15 | ≤35 |

IFNγ, IL-4 and TNFα production by SIL or CD4+ SIT was measured as described in Material and Methods. Data represents the mean and SD.
[1]2.0 × 10⁵ cells from psoriasiform lesions of 5-10 recipient scid/scid mice that had developed disease following reconstitution with CD4+/CD45Rb$^{hi}$ cells from normal BALB/c mice along with LPS and IL-12 were cultured for 48 hrs. Data is one value representative of 3 experiments showing similar values.
[2]2.0 × 10⁵ cells from the skin of 8-10 recipient scid/scid mice that did not show disease symptoms were cultured for 48 hrs. Data is from one experiment representative of 2 independent experiments showing similar values.
[3]2.0 × 10⁵ CD4+/CD45RB$^{hi}$ cells sorted by flow cytometry from spleen cells isolated from BALB/cj mice were cultured for 48 hrs. Cell purity ≥90%.

IFNγ-Deficient $CD4^+/CD45Rb^{hi}$ T Cells are Able to Induce Psoriasiform Lesions in scid Mice.

To examine whether IFNγ has a primary role in the induction of psoriasiform lesions, we first transferred naive T cells from IFNγ-deficient ($IFN\gamma^{-/-}$) mice into C.B-17 scid/scid mice. Interestingly, we found that despite the lack of IFNγ, $CD4^+/CD45Rb^{hi}$ T cells from $IFN\gamma^{-/-}$ donors were able to induce psoriasiform lesions in scid/scid mice. Disease induction occurred with similar frequency, but ear thickness in diseased $IFN\gamma^{-/-}$ T cell scid/scid mice was, on average, less than in control mice, and skin lesions on eyes and face were present, but were less pronounced. The average clinical score of the diseased mice was 0.9±1.0, and only one case of severe psoriasis (clinical score≥3) was noted. In addition, disease onset was delayed (10-12 weeks after cell transfer), when compared to control mice (average of 6-8 weeks after cell transfer). Consistent with these observations, it appeared that in particular the hyperkeratosis in the skin of $IFN\gamma^{-/-}$ T cell scid/scid mice was less pronounced.

The absence of donor derived IFNγ production was verified by testing the supernatants of isolated lymphocytes from the skin of diseased CD4+/CD45Rb$^{hi}$ IFNγ$^{-/-}$ reconstituted scid/scid mice after 48 hrs. of stimulation with anti-CD3 and anti-CD28. No detectable levels of IFNγ (<30 μg) were found in any of the samples when tested by ELISA (Table 3). The expression of TNF was also measured and found to be elevated, but significantly less than the TNFα levels observed in mice reconstituted with CD4+/CD45Rb$^{hi}$ T cells from wild-type animals (Table 3 or 4).

TABLE 4

Anti-IL-12 treatment reduces T cell inflammatory responses significantly, IFN-γ$^{-/-}$ inflammatory T cells produce TNF-α.

| T cell Source | IFNγ (pg) | IL-4 (pg) | TNFα (pg) |
|---|---|---|---|
| Control mice[1] | 56380 ± 7940 | 76 ± 5 | 698 ± 195 |
| Anti-IL-12 treated mice[2] | 300 ± 7 | 46 ± 4.1 | ≤35 |
| Mice reconstituted with CD4+/CD45RB$^{hi}$ IFNγ$^{-/-}$BALB/c T-cells[3] | ≤20 | 69 ± 7.3 | 122 ± 31 |

IFNγ, IL-4 and TNFα production by $2.0 \times 10^5$ SIL was measured as described in Material and Methods. Data represents the mean and SD. All mice were sacrificed at week 10 after T cell transfer. Control and treatment groups consisted of 4-5 mice. Lymphocytes from each group were pooled for in vitro stimulation regardless of disease status.
[1]Cells were isolated from psoriasiform lesions of 5-10 diseased scid/scid mice following reconstitution with CD4+/CD45Rb$^{hi}$ and LPS plus IL-12 administration. Mice did not receive any treatment. Data is from one experiment representative of 3 independent experiments showing similar values.
[2]Mice were treated twice i.p. with 0.5 mg of anti-IL-12 mAb (Clone C17.8 rat IgG$_1$ on day 7 and 35. Mice were sacrificed at week 10 after T cell transfer. Data is from one experiment representative of 2 independent experiments showing similar values.
[3]Cells isolated from psoriatic skin from the ears and eyelids of recipient scid/scid mice that were reconstituted with CD4+/CD45RB$^{hi}$ cell from BALB/cj IFNγ$^{-/-}$ mice.

To further rule out that minute levels of IFNγ secreted by host NK cells are sufficient to induce disease, we injected IFNγ$^{-/-}$ T cells into scid-beige mice. These mice carry in addition to the scid mutations, the beige mutation which causes a deficiency in NK cells in addition to the T, B cell deficiency already present in the scid mutation. Scid/beige mice that received IFNγ$^{-/-}$ CD4+/CD45Rb$^{hi}$ T cells also developed a very significant increase in ear thickness, however again, the onset of disease was significantly delayed and the incidence of disease was reduced (Table 5) when compared to mice that had received IFNγ$^{-/-}$ CD4+/CD45Rb$^{hi}$ T cells. In addition, the severity of disease as measured by ear thickness and clinical score (Table 5) was attenuated. Interestingly, despite the presence of severe mononuclear cell infiltration, the acanthosis, consistent with above results, was less pronounced in these animals. These results indicate that IFNγ regulates keratinocyte proliferation, but not mononuclear cell infiltration/activation in psoriasis.

TABLE 5

Incidence and clinical score of CD4+/CD45Rb$^{hi}$ scid mice

| T Cell/Recipient[1] | Incidence[5] | Average Clinical Score[6] | Severe Disease[7] |
|---|---|---|---|
| IFNγ+/+/scid/scid[2] | 9/10 (90%) | 2.4 ± 0.7 | 5/10 (50%) |
| IFNγ+/+/scid/scid α-IL-12[3] | 1/10 (10%) | 0.1 ± 0.3 | 0/10 (0%) |
| IFNγ+/+/scid/scid[4] | 5/9 (56%) | 0.9 ± 1.0 | 1/9 (11%) |
| IFNγ+/+/scid/beige[4] | 3/7 (43%) | 1.0 ± 1.3 | 2/7 (29%) |

[1]All mice were reconstituted with either IFNγ+/+ or IFNγ$^{-/-}$ CD4+CD45Rb$^{hi}$ T cells and LPS plus IL-12.
[2]Mice received either PBS or control Ab (rat IgG1).
[3]Antibody treatment is described in material and method and Table 3.
[4]Scid/scid and scid/beige mice that were reconstituted with CD4+/CD45 RB$^{hi}$ cell from BALB/cj IFNγ$^{-/-}$ mice.
[5]Disease incidence is reported as number of mice with disease over 10 weeks of time: criteria being ear thickness ≥26 nm or clinical score of ≥1.

TABLE 5-continued

Incidence and clinical score of CD4+/CD45Rb$^{hi}$ scid mice

| T Cell/Recipient[1] | Incidence[5] | Average Clinical Score[6] | Severe Disease[7] |
|---|---|---|---|

[6]Average clinical score ± SD was assessed of all mice in the group as described in material and methods, p versus IFNγ+/+scid/scid: anti-IL-12: p < 0.0000001, IFNγ$^{-/-}$scid/scid: p < 0.003, IFNγ$^{-/-}$ scid/beige: p < 0.01. Statistical analysis was performed using the two-tailed student t test.
[7]Severe disease induction calculated as the number of animals that received an average histology score of ≥2.5 and/or a clinical score of ≥3.

IL-12 is Highly Expressed in Psoriasiform Lesions and In Vivo Neutralization of IL-12 Downregulates TNFα and IFNγ and Inhibits Disease Development.

We next focused on IL-12, since this proinflammatory cytokine plays a key role in the induction of IFNγ. We performed immunohistochemical studies to detect the presence of heterodimeric IL-12 in inflamed tissue. There is a very significant amount of IL-12 (p35/p40, (p70)) heterodimer expressed in the tissue of diseased CD4+/CD45Rb$^{hi}$ treated mice. In contrast, significantly less staining could be observed in CD4+/CD45Rb$^{hi}$ treated animals that were injected with anti-IL-12 mAb (0.5 mg/mouse) on day 7 and 35.

To further evaluate the role of IL-12 in the induction of psoriasiform lesions, we administered anti-IL-12 mAb (0.5 mg) at day 7 and 35 after T cell transfer to scid/scid mice that had received wild type CD4+/CD45Rb$^{hi}$ T cells. Two doses of anti-IL-12 mAb were given to maintain a high enough Ab titer over the entire period of disease induction after the transfer of CD4+/CD45Rb$^{hi}$ T cells. In two independent experiments, mice (group of 5) that were treated with anti-IL-12 mAb were completely protected from developing disease. Only one mouse, out of 10, developed visible mild psoriasis in the form of slight hair loss and erythema around the eyelids (clinical score 1), however, this mouse and all other mice treated with anti-IL-12 mAb did not develop any increase in ear thickness. In contrast, control mice that were treated with rat IgG control antibodies or with PBS showed an incidence of 90% (9 out of 10 mice developed disease) with an average clinical score of 2.4±0.7. The higher incidence and severity of disease in this group was also associated with a significantly higher increase in ear thickness over time.

The ears and skin of mice that received anti-IL-12 were examined for the cytokine production of infiltrating lymphocytes. While there were very few lymphocytes present in the skin of anti-IL-12 treated animals, these were isolated and tested for IFNγ, IL-4 and TNFα production. Only low levels of IFNγ, IL-4 and TNFα were detected in the supernatants of cells isolated from treated animals when compared to the cytokine production of supernatants obtained from control animals (Table 4).

The results above are corroborated by the analysis of the histopathological sections obtained from animals that were treated with anti-IL-12 mAb. Mice that had been treated with 0.5 mg of anti-IL-12 mAb on day 7 and 35 lacked any signs of significant inflammation, acanthosis or hyperkeratosis. Thus, anti-IL-12 administration seems to prevent the development of psoriasiform lesions by inhibiting keratinocyte hyperproliferation and mononuclear cell infiltration most likely by downregulating both IFNγ and TNFα production.

Discussion

The above data demonstrates how immunomodulatory stimuli, in this case microbial antigens and the proinflammatory lymphokine IL-12, affect the ability of T cells to induce psoriasis in this newly developed CD4+/CD45Rb$^{hi}$ T cells transfer model. It is shown that co-administration of LPS and IL-12 (1 and 10 ng) led to a more rapid onset and to an increased incidence of psoriasis in C.B-17 scid mice. In addition, the observed lesions in treated mice were also more severe. In additional experiments, it was demonstrated that co-administration of SEB also led to a significant increase in disease incidence and expression. These findings suggest the importance of bacterial or viral infections before the appearance of psoriasiform lesions. Most notably, the skin lesions that developed by this method of induction were characteristic and remarkably similar to human psoriatic lesions, exhibiting most clinical and histological hallmarks. The scaling and thickening of skin evident macroscopically was due to marked hyper-, parakeratosis and acanthosis. It is further documented in the microscopic appearance of rete pegs, ulcer and pustule formation and the often severe epidermal hyperplasia. The inflammatory cell infiltration was primarily mononuclear and composed of lymphocytes with fewer monocytes, macrophages and plasma cells. Moreover, the majority of CD4+ T cells isolated from psoriasiform lesions express low levels of CD45Rb, which is consistent with the fact that recent studies in humans found that T cells isolated psoriatic plaques exhibit a memory phenotype. Beside the similarity to the human histology observed in this study, there are also some differences. Most notable is the absence of CD8+ T cells in the epidermis of psoriatic plaques, which can be found in human psoriasis. So far, however, a primary role for CD8+ T cells in the pathophysiology of psoriasis has not been identified and successful initial therapies targeting CD4+ T cells rather than CD8+ T cells point toward the CD4+ T cells as the primary culprit of the disease.

Several mechanisms could be responsible for the disease-promoting effects of LPS, IL-12 and SEB. First, these immunomodulators may assist in the proliferation and differentiation of naïve Th0 cells to Th1 cells. Recent studies have shown that microbial products such as LPS can directly stimulate TNFα, IL-6 and to a lesser extent IL-12 production by murine skin-derived dendritic cells; and thus may be responsible for setting the proinflammatory condition for autoreactive T cells. CD45Rb$^{hi}$ T cells after the transfer into SCID mice require additional IL-12 dependent signals in order to develop into autoimmune effector cells.

In addition to their immunostimulatory effects on macrophages and their effects on the development of Th1 effector cells, LPS, IL-12 and SEB may also modulate leukocyte trafficking in recipient mice to result in the cutaneous localization of Th1 effector cells. LPS promotes leukocyte recruitment by stimulating endothelial cell expression of E-selectin, ICAM-1, and VCAM-1 adhesion molecules both directly and through its ability to induce the production of IL-1, TNF-α and IFN-γ. The proinflammatory effects of these cytokines on leukocyte adhesion and migration is also well-known.

IFNγ and IL-12 are two very important immunoregulatory cytokines, that have been shown to play an important role in the development of autoimmune disorders. IL-12 primarily activates NK and T cells; while IFNγ primarily activates macrophages and induces the upregulation of class II molecules on tissue cells. One might have expected IFNγ to be crucial for the induction of autoimmune effector cells in psoriasis. The above data, however, indicate that IFNγ may only participate in the disease process by enhancing disease severity, most likely by promoting keratinocyte proliferation, but clearly not by inducing and maintaining pathogenic, inflammatory T cells in psoriatic skin. This is supported by the fact that the histology observed in lesions of mice that received IFNγ$^{-/-}$ donor T cells showed slightly lesser or equal signs of inflammation but hyperkeratosis or acanthosis was clearly diminished in scid/scid or scid/beige mice. Moreover, although clinical severity of disease, as measured by ear thickness and macroscopic observation, was attenuated when compared to control animals, the penetrance of disease was very similar. This was also found to be true when IFNγ$^{-/-}$ T cells were transferred into T, B- and NK cell deficient scid/beige mice.

These results indicate that IFNγ is an important co-factor in the induction of aberrant keratinocyte proliferation.

The absence of host-derived IFNγ was verified by the measurement of IFNγ from anti-CD3 and anti-CD28 stimulated whole cells isolated from the inflammatory lesions of animals that received IFNγ$^{-/-}$ T cells. As expected, we were unable to detect any measurable level of IFNγ, thus further ruling out the possibility that IFNγ might be secreted by non-T cells in the skin, including NK-cells.

In contrast to IFNγ, an absolute requirement for IL-12 in the development of chronic psoriasiform lesions in scid/scid mice was demonstrated by several observations made in these studies. First, medium and low doses of IL-12 (1 and 10 ng/mouse) administered following donor T cell transfer resulted in a higher incidence and severity of disease. Moreover, in situ staining of inflamed tissue revealed a significant present of heterodimeric IL-12 (p70), while IL-12 staining was not present at all in non-inflamed control tissue. Most importantly, in vivo neutralization of IL-12 with a mAb reacting against IL-12 p70 heterodimer 7 days following T cell transfer was able to completely abrogate disease induction. An interesting aspect of these studies was that high doses of IL-12$^-$ (100 ng/mouse) inhibited disease induction instead of promoting disease development.

In summary, the chronic skin disorder described in this study included features that are normally only observed in human psoriasis, such as rete pegs, severe acanthosis and infiltration of Th1 cells into the dermis. The clinical and histopathological abnormalities were greatly enhanced by the in vivo administration of LPS and IL-12, demonstrating an important role of infectious agent(s) in the pathogenesis of the disease. Moreover, it is demonstrated for the first time that the induction of psoriasiform lesions was dependent on IL-12, but independent of IFN-γ. These results provide insight into the specific pathogenic requirements of Th1 promoting cytokines and cells for the development of psoriasiform lesions, and into the prevention and treatment of psoriasis in humans.

Example 2

Animals were tested for the effect of treatment with antibodies to IL-12 on on-going and late-stage psoriatic disease. The disease was induced by the methods described in Example 1, i.e., using 3×10$^5$ CD4+ CD45Rb$^{hi}$ cells transferred into scid/scid mice followed by injection of LPS and IL-12. Treatment with the anti-IL-12 antibody was always at 1 mg/mouse/dose. The results of four separate experiments are shown in FIG. 1. In the initial experiment, (n=5 untreated; n=2 treated), the mice received injections of anti-IL-12 at weeks 9 and 10 (i.e., about 5 weeks after the appearance of psoriatic symptoms) and were sacrificed for histology at week 14. Whereas the untreated mice had an average histology score of 2.5, indicating moderate to high symptoms, the treated mice had a histology score of only 0.25, indicating almost no symptoms. Hence, two injections of the anti-IL-12 antibody were highly effective in alleviating established symptoms of psoriasis.

In a second experiment, 3 groups of mice were either left untreated, treated 11 with an isotype-matched control antibody not binding to IL-12, or treated with the anti-IL-12 antibody (n=4 for each group). Treatment was at weeks 9 and 10, and histology specimens were taken at week 12. Again, the untreated or control-treated mice had substantial levels of psoriatic symptoms, and the anti-IL-12 treated mice had much lower levels. In a third experiment, mice were untreated (n=5) or treated with anti-IL-12 at weeks-9 and 10 (n=−6), but half the treated mice were sacrificed for histology at week 12 as before, and half later at week 17. The treated mice again showed a dramatic reduction in histology score, which was largely maintained at week 17, seven weeks after treatment was stopped.

Finally, in a fourth experiment (n=4 for groups treated with anti-IL-12 and isotype-matched control antibody), treatment was not initiated until week 14, about weeks after psoriatic symptoms appeared, so the symptoms were very well-established (ear thickness≥40 µm). Treatment was weekly from weeks 14 through 17. Despite the well-established disease, anti-IL-12 treatment was dramatically effective in reducing the symptoms (to average histology score 0.25). This result was confirmed by weekly measurement of ear thickness, an independent measure of disease severity, as shown in FIG. 2.

By combining all these experiments, the average histology score of the untreated or control-treated mice at sacrifice was 2.53, whereas the average histology score of the mice treated with anti-IL-12 antibody was only 0.65, a highly statistically significant result ($p=1.7 \times 10^{-9}$ by Student's two-tailed t-test).

What is claimed is:

1. A method of treating a patient suffering from psoriasis comprising the step of administering to the patient a therapeutically effective amount of an antibody that binds to interleukin 12 (IL-12).

2. A method for treating a patient suffering from psoriasis consisting of administering to the patient an effective amount of a therapeutically active agent consisting essentially of an antibody that binds interleukin 12.

3. The method according to claim 2, wherein said antibody is a monoclonal antibody.

4. The method according to claim 2, wherein said antibody neutralizes interleukin 12.

5. The method according to claim 2, wherein said antibody is administered orally, topically, or parenterally.

6. The method according to claim 2, wherein said antibody is administered subcutaneously, intramuscularly, or intravascularly.

7. A method of treating a patient suffering from psoriasis comprising the step of administering to the patient a therapeutically effective amount of an antibody that binds to interleukin 12, wherein said antibody neutralizes interleukin 12.

* * * * *